(12) United States Patent
Torres Simón

(10) Patent No.: US 6,936,726 B2
(45) Date of Patent: Aug. 30, 2005

(54) FLAVANOL AND CYSTEAMINE CONJUGATES

(75) Inventor: José Luis Torres Simón, Barcelona (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 10/451,475

(22) PCT Filed: Dec. 14, 2001

(86) PCT No.: PCT/ES01/00485

§ 371 (c)(1),
(2), (4) Date: Dec. 3, 2003

(87) PCT Pub. No.: WO02/051829

PCT Pub. Date: Jul. 4, 2002

(65) Prior Publication Data

US 2004/0077711 A1 Apr. 22, 2004

(30) Foreign Application Priority Data

Dec. 22, 2000 (ES) .......................................... 200003093

(51) Int. Cl.[7] ..................... C07D 311/78; C07D 309/00; C07D 311/94; A61K 31/535; A01N 43/00
(52) U.S. Cl. ....................... 549/401; 549/356; 549/381; 549/396; 514/183; 514/228.8; 514/229.5; 514/230.5; 514/230.8
(58) Field of Search .......................................... 549/200

(56) References Cited

FOREIGN PATENT DOCUMENTS

JP           01025726         1/1989

OTHER PUBLICATIONS

Abstract of "Journal of Agricultural Food Chemistry, Oct. 2001, 49(10): 4627–37".*
Abstract of "Organic Letters, Nov. 25, 2004, 6(24): 4583–6".*

Torres et al., DN 135:3708587 abstract of New Flavanol Derivatives from Grape Byproducts, Sep. 13, 2001, Journal o Agricultural and Food Chemistry (2001), 49(10), 4627–4634.*

Patent Abstract of Japan of JP 01025726 Dated Jan. 27, 1989.

Torres, J.L., et al. "New flavanol derivatives from grape (Vitis vinifera) by products . . ." *Journal of Agricultural and Food Chemistry*–American Chemical Society (2001) vol. 49, No. 10, pp. 4627–4634.

Torres, J.L., et al. "Chromatographic Characterization of Proanthocyanidins after Thiolysis with Cysteamine" *Chromatographia* (2001) vol. 54, No. 7/8, pp. 523–526.

Wirth, C., et al. "Pharmacologically active Procyanidines from the bark of Uncaria tomentosa" *Phytomedicine* (1997)vol. 4, No. 3, pp. 265–266.

Facino, R.M., et al. "Free Radicals Scavenging Action and Anti–enzyme Activities . . . " *Arzneim–Forsch* (1994) vol. 44, No. 5, pp. 592–601.

* cited by examiner

*Primary Examiner*—Sabiha N. Qazi
(74) *Attorney, Agent, or Firm*—Ladas & Parry LLP

(57) ABSTRACT

The present invention refers to new products generated by the conjugation of flavanols with molecules that contain the thiol group. New molecules are obtained from polyphenolic plant extracts rich in oligomeric and polymeric procyanidines and prodelfinidins. In this way, new products are generated with antioxidant properties for application as protective agents for the organism against disorders such as cancer, cardiovascular diseases and premature aging. The invention also refers to obtaining these new agents from waste material generated by the agroalimentary industry. Since these waste materials are highly complex mixtures a simple and effective method is described to isolate and purify these, based on the physico-chemical characteristics of the new molecules.

15 Claims, 3 Drawing Sheets

R₁ = H (catechines) OH (galocatechines)

R₁ = H (procyanidines), OH (prodelfinidines)

R₁ = H (catechines) OH (galocatechines)

R₁ = H (procyanidines), OH (prodelfinidines)

I  $R_1$=H, $R_2$=H, $R_3$=OH, 4ξ-(2-aminoethylthio)epicatechine

II  $R_1$=H, $R_2$=OH, $R_3$=H, 4ξ-(2-aminoethylthio)catechine

III  $R_1$=H, $R_2$=H, $R_3$=Gal, 4ξ-(2-aminoethylthio)epicatechine-3-O-galate

IV  $R_1$=OH, $R_2$=H, $R_3$=OH, 4ξ-(2-aminoetiltio)epigalocatechine

V  $R_1$=OH, $R_2$=OH, $R_3$=H, 4ξ-(2-aminoethylthio)galocatechine

VI  $R_1$=OH, $R_2$=H, $R_3$=Gal, 4ξ-(2-aminoethylthio)epigalocatechine-3-O-galate

FLAVANOL AND CYSTEAMINE CONJUGATES

SECTOR OF THE TECHNIQUE

This invention concerns new products that result from the conjugation of flavenols with molecules that contain the thiol group. The new molecules are obtained from polyphenolic plant extracts rich in oligomeric and polymeric procyanidines and prodelfinidins. In this way, new products are generated with antioxidant properties and application as protective agents for the organism against disorders such as cancer, cardiovascular diseases and premature aging. The invention also refers to obtaining these new agents from waste materials from the agroalimentary industry. These waste materials are very complex mixtures and a simple and effective method of isolation and purification is described based on the physico-chemical characteristics of the new molecules.

BACKGROUND OF THE INVENTION AND STATE OF THE ART OF THE TECHNIQUE

Flavanols are members of a larger family of compounds called polyphenols. These contain more than one hydroxyl group (OH) bonded to the corresponding benzene ring. Oligomeric flavenols include procyanidines and prodelfinidines depending on whether these present two or three hydroxyl groups in the B ring of the flavenolic structure, respectively. FIG. 1 shows the general structure of procyanidines and prodelfinidins. Polyphenols and, more specifically, flavenols are present in all aerial parts of plants and are found in high concentrations in skin, bark and seeds. Sources rich in polyphenols are leaves of the tea plant, grape skin/pips and pine bark. The antioxidant/antitiradical action of polyphenols makes them useful as products for the prevention of diseases and health promotion. Body cells are constantly exposed to so-called reactive oxidant species (ROS) such as hydrogen peroxide ($H_2O_2$), superoxide anion ($O_2^{+-}$), hydroxyl radical ($OH^+$) and peroxide radicals ($ROO^+$), which have the potential to cause cellular damage. For example, damage of genetic material (DNA) can cause mutations and cancer, and alterations in blood proteins (low-density lipoproteins, LDL) can lead to lipid accumulation and consequent blockage of arteries. In the skin, lipidic oxidation of the cell wall is related to changes in permeability which cause dryness and premature aging. Most ROS are produced during ordinary biological processes and the organism avoids these harmful effects using its own defense mechanisms (e.g. superoxide dysmutase, catalase and glutathione peroxidase against superoxide anion, hydrogen peroxide and organic peroxides, respectively). However, defense systems are not perfect and some of the reactive oxidant species can evade these. Moreover, some diseases, aging or external factors such as environmental pollution, tobacco and ultraviolet radiation can produce ROS levels that exceed the defense mechanisms' capacity. In these cases, an additional preventive action is required using exogenous antioxidants. For information about ROS, oxidative damage, defense mechanisms and the function of polyphenols and other antioxidants, see Diplock, A. T., Charleux, J. L., Crozier-Willi, G., Kok, F. J., Rice-Evans, C., Roberfroid, M., Stahl, W., Vina-Ribes, J., Br. J. Nutr., 80 Suppl 1, 77–112 (1998). Natural extracts of procyanidine have been described with antioxidant activity [Pietta, P., Simonetti, P., Mauri, P., J. Agr. Food Chem., 46 (11), 4487–4490 (1998); Masquellier, J., U.S. Pat. No. 4,698,360; Frangi, E., Bertani, M., Mustich, G., Tuccini, G., U.S. Pat. No. 5,484,594; Nafisi-Movaghar, K., Seroy, W. A., Svanoe, T. T., U.S. Pat. No. 5,912,363] and some of these are currently on the market.

Polyphenols also present other interesting activities, some of which are related with their adhesive/antiadhesive properties. Hence, polyphenols and especially oligomeric flavenols and glycosylated flavenols present antimicrobial activity at least partially due to inhibition of bacterial adhesion Walker, E. B., Mickelsen, R. A., Mickelsen, J., U.S. Pat. No. 5,646,178; Walker, E. B., Mickelsen, R. A., Mickelsen, J., U.S. Pat. No. 5,650,432; Hamada, S., Kontani, M., Hosono, H., Ono, H., Tanaka, T., Ooshima, T., Mitsunaga, T., Abe, I., FEMS Microbiol Lett., 143 (1), 35–40 (1996)]. Polyphenols and their derivatives are also used in the food industry as preservatives.

A large proportion of polyphenolic extracts on the market are mixtures of many species with different degrees of polymerization. It is not known for most products how the different components of mixtures are absorbed and distributed in the different systems and biological tissues. Often, some of the active molecules are lost due to their tendency to aggregate among themselves or with proteins, processes that cause their deactivation for example in the skin or the digestive system. Moreover, researchers found that not only polyphenols, especially oligomeric ones, have a general biological activity but also different fractions or individual species of oligomeres have differentiated biological potentials. Owing to the similarity of their physico-chemical properties, the individual compounds are difficult to purify. Moreover, normally the amount of a selected oligomeric compound in a complex mixture is small.

Thioacidolysis of procyanidines and prodelfinidines is used to establish the degree of polymerization of oligomeric mixtures [Rigaud, J., Pérez-Ilzarbe, J., Ricardo da Silva, J. M., Cheynier, V., J. Chromatogr., 540, 401–405 (1991); Prieur, C., Rigaud, J., Cheynier, V., Moutounet, M., Phytochemistry, 36 (3), 781–784 (1994); Souquet, J.-M., Cheynier, V., Brossaud, F., Moutounet, M., Phytochemistry, 43 (2), 509–512 (1996), Souquet, J. M., Labarbe, B., LeGuerneve, C., Cheynier, V., Moutounet, M., J Agr. Food Chem., 48 (4), 1076–1080 (2000)]. Toluene-α-thiol is used as a source of thiols. Terminal flavan-3-ols are released as such while the internal polymer units are released as benzylthioethers in position 4 of the flavanolic system. The mixtures are studied by reverse phase high performance liquid chromatography, RP-HPLC). This method is useful from an analytical perspective. Applications have not been described for the resulting derivatives and also the breakdown product, Toluene-α-thiol, is toxic, irritant and lacrimogenous. The purification procedure only consists of reverse phase chromatography.

There is one example of cysteamine conjugates with an antioxidant molecule (tocopherol) [Pelle, E., Maes, D. H., U.S. Pat. No. 5,811,083]. Cysteamine is joined to tocopherol by an amide bond thus eliminating the amino function. Moreover, tocopherol is a different type of compound to flavan-3-ols. There are also examples of antioxidant compounds obtained by adding mercaptoethanol and alkylic chains to flavanols [Tanaka, T., Kusano, R., Kouno, I., Bioorg. Medicinal Chem. Letter, 8 (14), 1801–1806 (1998)]. These are derivatives that do not contain the amino group and have an amphyphylic character.

DESCRIPTION OF THE INVENTION

The present invention describes a new combination of a species that contains a thiol group and an amino group with species that include the flavan-3-ol system. It also describes a method to obtain and purify new products. The thiol is cysteamine and the polyphenolic part consists of different monomers derived from polymeric procyanidines and prodelfinidins. FIG. 2 shows the structures of the new conjugates. The polyphenol source can be any plant material that contains procyanadins and/or prodelfinidines regardless of their degree of polymerization. One aspect of the invention uses a byproduct of grape pressing as a source of polymeric polyphenols. After a simple thioacidolysis step, the new molecules are effectively isolated from the mixture by a process of cationic exchange, thanks to the amino group introduced with the cysteamine. Ulterior purification by reverse phase chromatography produces each of the active compounds. Flavanolic conjugates are dried at low pressure.

Figure 1:
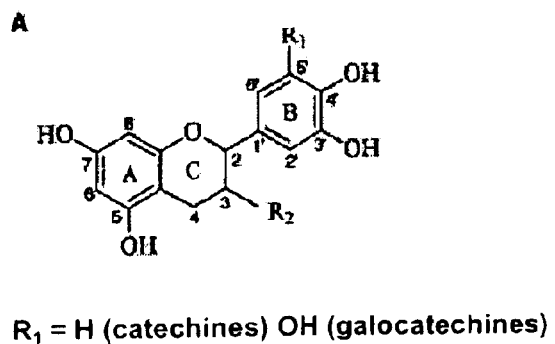
FIG. 1. Monomeric and polymeric flavan-3-ol structures. A: Monomeric flavan-3-ols. B: Oligomeric and polymeric procyanidines and prodelfinidins. The arrows indicate possible polymerization positions. The bonded molecules can be monomeric or oligomeric flavanols. The bonds are established between the central type C ring and either of the two positions available in the A type rings.
Figure 1:
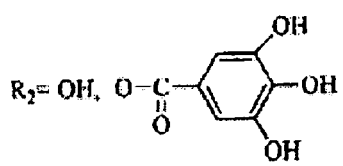
Figure 1:
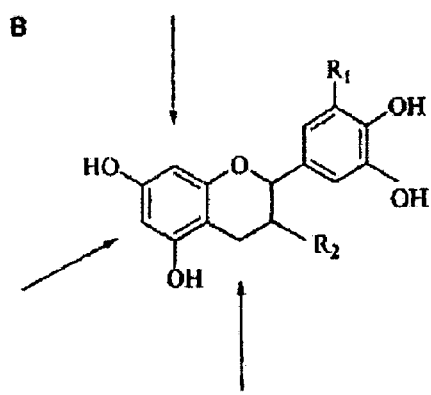
Figure 1:
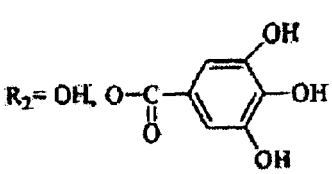

| | | |
|---|---|---|
| □ | Trolox | |
| ◇ | Epicatequina | |
| ○ | Aminoetiltioepicatequina 1 | |
| △ | Aminoetiltioepicatequina-3- | O-galato III |

DETAILED DESCRIPTION OF THE INVENTION

The present invention describes the conjugation of polymeric polyphenols with cysteamine to produce products I–VI. The first source of oligomeric and polymeric flavenols is treated with water/ethanol to obtain the crude polyphenolic fraction. It is not necessary to carry out subsequent fractioninations since thioacidolysis works with the first extract. This does not exclude the use of other fractions of variable purity obtained from the first extract or during any other similar process. In the course of the present invention, aminoethyl derivatives I–VI have been generated from fractions of the first extract. After eliminating water and extraction solvents, the residue is suspended in methanol in the presence of hydrochloric acid and a suitable amount of cysteamine. The mixture is heated to 65° C. and after 15 min, is cooled and diluted with water. This diluted solution is directly loaded onto a cation-exchange column equilibrated at a slightly acid pH. The flavan-3-ols conjugated with cysteamine are retained by the resin while the rest of the material, i.e. monomeric flavan-3-ols, other polyphenols such as flavonols and phenolic acids, and other species such as sugars, are eliminated in the washing process. After, the derived products are recovered from the column in the presence of a suitable amount of salt (sodium chloride) and organic solvent by an efficient and simple procedure. The resulting mixture, which contains a much smaller amount of products than the crude reaction mixture, is submitted to another purification by reverse phase liquid chromatography followed by lyophilization to obtain each of the new molecules with a purity of over 99.5% by analytical HPLC.

The new molecules are potent antioxidants with an excellent capacity to capture free radicals. The conjugates are more efficient than Trolox (water-soluble analogue of Vitamin E) in the DPPH assay (1,1-diphenyl-2-picrylhydracil) [Brand-Williams, W., Cuvelier, M. E., Berset, C., Lebensm.-Wiss. u.-Technol., 28, 25–30 (1995)]. The conjugates are also more efficient than the corresponding non-derived species.

The method of the present invention includes a number of phases that are presented below separately to clarify the explanation.

Extraction Phase

The first step in the preparation of the new conjugates is extraction of polyphenols from the first plant source. In one of the applications of the invention, polyphenols are extracted from the grape-pressing residue (skin, pips and lees) with water/ethanol (3:7) to give a crude C extract. The same procedure can be used with other sources such as the pods, skins/seeds of other species and leaves. Other extraction solvents miscible with water such as methanol and acetone can be used. In another application of the invention, the first crude extract (C) is fractionated by liquid/liquid distribution using ethyl acetate and water acidified with acetic acid. The mixture was separated into two layers, the organic layer (O, mainly ethyl acetate) and the aqueous layer (A, mainly water). The organic fraction O mainly contains monomeric flavan-3-ols ((+)-catechine, (−)-epicatechine, (−)-epicatechine-3-O-galate), oligomeric procyanidines and prodelfinidines and glycosylated flavanols. The aqueous fraction A mainly contains procyanidines and prodelfinidines with a high degree of polymerization and flavonols and other non-falvonolic species such as sugars. All the crude products and fractions are analyzed by reverse phase HPLC with elution by water mixtures and acetonitrile in the presence of 0.1% trifluoroacetic acid with detection at 214, 280 and 320 nm.

Thiolysis Phase

Figure 2:
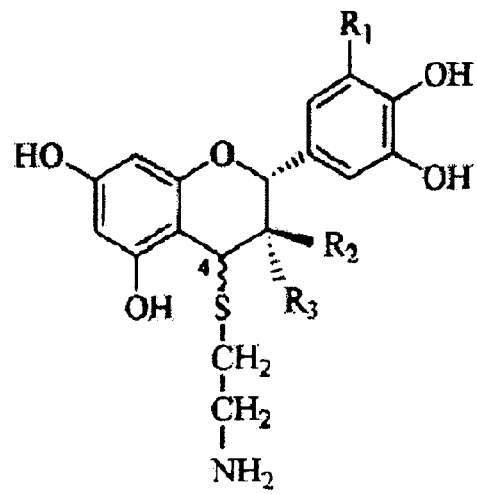
FIG. 2. Structures of new aminoethyl derivatives of flavan-3-ols.
Figure 2:
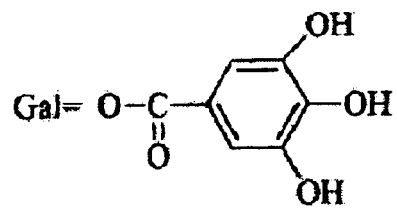

The second step is thioacidolysis of the first extract and the fractions depending on the case. Several of the mixtures have been used for this purpose to i.e. the crude ethanolic extract C, the ethyl acetate fraction O and the aqueous fraction A obtained in the previous phase. It is of special interest for the present invention that the final products can be obtained efficiently regardless of the purity of the sources of procyanidins/prodelfinidins. All the starting mixtures in this phase are lyophilized before the hydrolysis treatment. The thiolysis reaction has been described to be complete in 10–15 min at 65° C. in the presence of 0.2 M hydrochloric acid in methanol and a surplus of thio, of approximately 1:50 (weight/weight). In the present invention, a ratio of reagents of only 1:5 has been used and the initial polymers were consumed in only 15 minutes. Formation of anthocyanines has not been detected, as revealed by the absence of signals in the analytical chromatogram register of HPLC at 525 nm. Majority conjugates in the mixture resulting from thiolysis are epicatechine thioethers (I), epicatechinegalate (III) y catechine (II), in order of abundance. Other minority products are derivatives of epigalocatechine (IV), epigalocatechinegalate (VI) and galocatechine (V). The configuration of compounds in position 4 of the C ring could correspond to either of two possibilities (4α, 4β). In FIG. 2, the configuration in this carbon is expressed as 4ξ.

Isolation and Purification

A crucial aspect of the present invention is isolation of the flavanol derivatives from the complex reaction mixtures. In this stage it is an important advantage to have introduced an amine group during formation of the conjugates. The new derivatives are retained electrostatically to a cationic exchange resin while the rest of the material is eliminated in the resin washing. This operation is important because it permits one to work with first extracts without requiring later fractionating. It is to little avail that these are useful in the previous phase if the following purification is ineffective. Isolation of the new products can be done in the presence of a wide range of materials of different physico-chemical nature, which, while they are not retained in the resin by a positive charge, are easily eliminated in the washing process. It must be emphasized that most potential compounds for use as crude mixtures are of a non-ionic or anionic nature (negative charge in the working pH). The purification of individual compounds from the thiolysis mixture is greatly facilitated with this step. This washing process using resin presents a high efficacy that is independent of the extract or fraction used in previous stages. The composition of the thiolysis mixtures presents some variations depending on the starting material used and the majority products are essentially the same in all cases.

Different cationic exchange resins can be used in this isolation or washing stage. The resins preferentially include a sulphonic group incorporated in a polmeric support. There are several types of support that can be used in this stage of the invention. These include agarose, co-polymers of styrene-divinylbenzene, polyether and methacrylate. All the resins mentioned are strong exchangers (the anion is a strong acid). However, the possibilities are not limited to these supports or to the anion exchanger, which can also be, for example, a carboxyl group (weak acid) incorporated to an insoluble support. Preferentially, the conjugates are isolated on strong exchangers SP Sepharose®, supplied by Amersham-Pharmacia Biotech and MacroPrep HighS®, supplied by BioRad. The resins, column packed, are equilibrated with sodium acetate buffer at pH 4.75 in the presence of a quantity of water-soluble solvent, selected from methanol, ethanol, acetonitrile and tetrahydrofurane. The crude products of thiolysis are loaded in the column after diluting the reaction mixture with water (dilution factor 1/5). After, the resin is washed with 10 column volumes of the buffer eluent/equilibrium solvent system. The conjugates with cysteine are eluted from the resin sequentially using acetate buffers that contain appropriate quantities of solvent and salt (NaCl). The procedure not only allows the conjugates to be isolated but also provides separation between some of them, facilitating the subsequent purification operations even more.

Each of the individual chemical species is purified extensively by preparative reverse phase HPLC, preferably in a 25×5 cm column packed with stationary phase VYDAC® C18 provided by The Separations Group. The solutions obtained after washing/isolation are diluted with water (dilution factor 1/3) and separately loaded in the column, previously equilibrated with triethylamine phosphate buffer pH 2.25. Each component is eluted from the column using the appropriate amount of acetonitrile in the equilibrated buffer. After, the pure products are desalinated by packing them in the same column and eluting with water/acetonitrile in the presence of 0.1% trifluoroacetic acid. The final preparations are obtained by lyophilization.

Antioxidant/antiradical Power Assay

Figure 3:
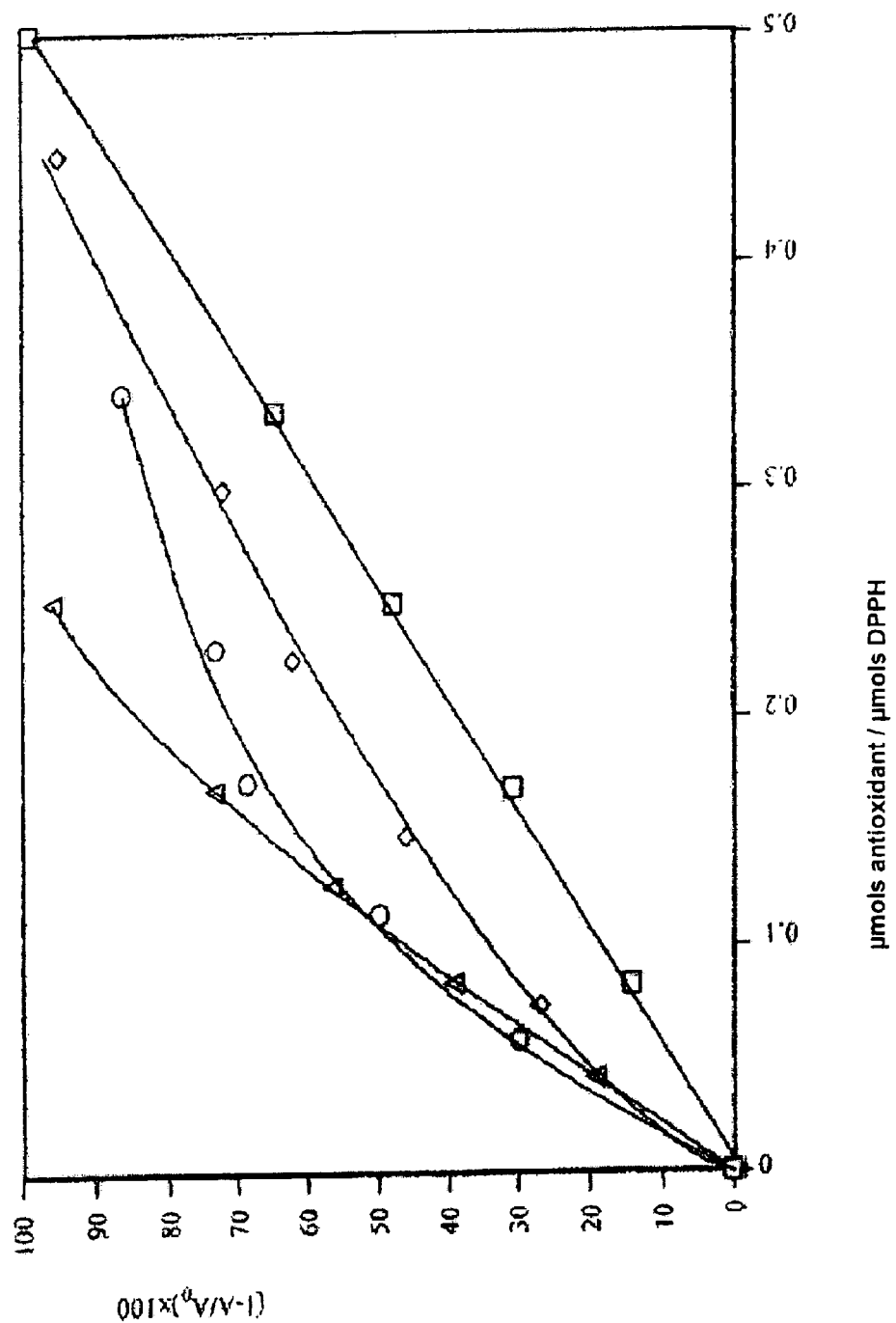
FIG. 3. Antioxidant efficacy of phenolic compounds in the DPPH assay. The absorbance (A) at 517 nm is a measure of the amount of free radical remaining in solution. $(1-A/A_0) \times 100$ represents the percentage of DPPH that has reacted with the antioxidant. The amount of antioxidant expressed as micromoles per micromole of initial DPPH• to correct the possible day to day variation in the amount of initial DPPH• The initial concentration of DPPH• is calculated from the absorbance (A) and a calibration line. Each point represents the mean of three determinations.

The new pure products are strong antioxidants/capturers of free radicals. FIG. 3 presents the results of the DPPH test (1,1-diphenyl-2-pycrylhydracil). The values of $EC_{50}$ (effective concentration 50) are calculated from the curves. $EC_{50}$ is the amount of antioxidant required to reduce the initial concentration to half (around 60 $\mu$M) of DPPH•. This amount is expressed as micromoles antioxidant/micromoles initial DPPH•. The $EC_{50}$ values for compounds relevant to the present invention are: Trolox (water-soluble analogue of Vitamin E), 0.26; (−)-epicatechine, 0.19, 4ξ-(2-aminoethylthio)epicatechine I, 0.11; 4ξ-(2-aminoethylthio) epicatechinegalate III, 0.11. According to the definition of $EC_{50}$, the most effective compounds are those with the lowest effective concentration.

EXAMPLE

In one application of this invention, compound I, 4ξ-(2-aminoethylthio) epicatechine is obtained by thioacidolysis of a water-soluble fraction (A). Fraction A contains a polyphenol concentration of 10 g/L, measured by the Folin-Ciocalteu method and expressed as equivalents in gallic acid. An aliquot of fraction A (80 mL, 0.8 g equivalents gallic acid) is evaporated under vacuum and suspended in methanol (80 mL). After, a solution of hydrochloric acid is added (HCl) 37% (1.72 mL) and cysteamine (4 g) in methanol (80 mL) and the mixture (160 mL) is maintained at 65° C. for 20 minutes and occasionally stirred. At the end of the reaction, water is added (640 mL) and the mixture is kept at 5° C.

Isolation of the aminoethylthioethers of the 3-flavanols is achieved by column cation exchange. The chromatographic column (1.6×10 cm, 20 mL bed volume), packed with HighLoad SP Sepharose® is equilibrated with 20 mM sodium acetate buffer, pH 4.75/acetonitrile($CH_3CN$) (9:1). The mixture (in aliquots of 120 mL) is loaded in the column and the underived material that does not contain the amino group is eluted with 10 bed volumes (200 mL) of equilibrated buffer. Compound I is eluted with a salt gradient (NaCl) (0 to 1 M) and a simultaneous gradient of $CH_3CN$ (10 to 20%) in 20 bed volumes (400 mL). The chromatographic process is repeated six times until all the thiolysis mixture has been exhausted. The fractions are analyzed by reverse phase HPLC in a C18 column and the eluents are mixtures of water/$CH_3CN$ in the presence of 0.1% trifluoroacetic acid. The fractions containing compound I are combined (650 mL for all the six loads) and diluted to 2.2 L with triethylamine phosphate buffer pH 2.25. The solution is loaded in a column prepacked with VYDAC® C18 (reverse phase) and compound I is eluted with a gradient of $CH_3CN$ (0 to 12%) in phosphate buffer of triethylamine pH 2.25 for 60 min. The compound 4ξ-(2-aminoethylthio) epicatechine I elutes at a value of 5–6% $CH_3CN$. The fractions that contain I are combined, diluted with water and desalinated using a fast gradient of $CH_3CN$ in 0.1% trifluoroacetic acid. The remaining solution (300 mL) is lyophilized to achieve a white solid (203 mg). The purity of the final product is higher than 99.5% by analytical HPLC with detection at 215 nm. Using mass spectroscopy with electrospray ionization, a molecular ion with 366.3 mass units is detected., when the theoretical ion for this structure is 366.1. The structure of I is confirmed by desulphuration with Raney nickel and comparison with a standard of (−)-epicatechine. The final product is also characterized by proton Nuclear Magnetic Resonance ($^1$H-NMR). Assignations ($\delta_H$) to 300 MHz in $(CD_3)_2CO$: 2.9–3.8 (4H, m, S—$CH_2$—$CH_2$—N); 4.02–4.07 (1H, 2m, 3-H); 4.08–4.18 (2H, m, S—$CH_2$—$CH_2$—$NH_2$); 4.10–4.22 (1H, m,d J=2.1 Hz, 4-H); 5.12–5.23 (1H, 2s, 2-H); 5.89 (1H, d J=2.4 Hz, 6-H); 6.07–6.09 (1H, 2d,J=2.4 Hz each, 8-H); 6.83 (2H, m, 5'-H, 6'-H); 7.10 (1H, d J=2.1 Hz, 2'-H). Assignations ($\delta_H$) to 300 MHz en $D_2O$: 2.64–3.26 (4H, 3m, S—$CH_2$—$CH_2$—N); 3.77 (1H, s width, 3-H); 3.91 (1H, s width, 4-H); 5.11 (1H, s width, 2-H); 5.84 (1H, d width, 6-H); 5.89 (1H, d width, 8-H); 6.72 (2H, s width, 5'-H, 6'-H); 6.82 (1H, s width, 2'-H). Some multiplicities detected could be due to the existence of two products with 4α, 4β configuration.

What is claimed is:

1. A compound having the following formula I or a salt thereof:

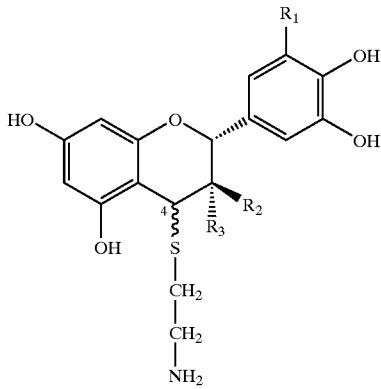

where $R_1$=H, $R_2$=H, $R_3$=OH, and the compound is a 4ξ-(2-aminoethylthio)epicatechine.

2. A product comprising (a) the compound of claim 1, wherein the compound is a 4-α-(2-aminoethylthio) epicatechine, and (b) a 4-β-(2-aminoethylthio) epicatechine of formula I or a salt thereof.

3. A compound having the following formula II or a salt thereof:

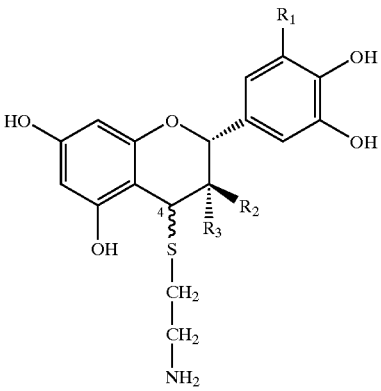

where $R_1$=H, $R_2$=OH, $R_3$=H, and the compound is a 4ξ-(2-aminoethylthio)catechine.

4. A product comprising (a) the compound of claim 3, wherein the compound is a 4-α-(2-aminoethylthio) catechine, and (b) a 4-β-(2-aminoethylthio)catechine of formula II or a salt thereof.

5. A compound having the following formula III of a salt thereof:

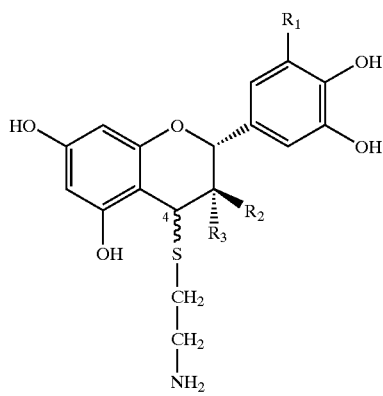

where $R_1$=H, $R_2$=H, $R_3$ is

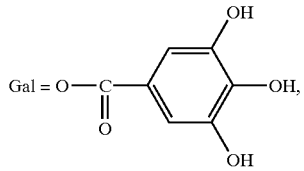

and the compound is a 4ξ-(2-aminoethylthio)epicatechine-3-O-galate.

6. A product comprising (a) the compound of claim 5, wherein the compound is a 4-α-(2-aminoethylthio) epicatechine-3-O-galate, and (b) a 4-β-(2-aminoethylthio) epicatechine-3-O-galate of formula III or a salt thereof.

7. A compound having the following formula IV or a salt thereof:

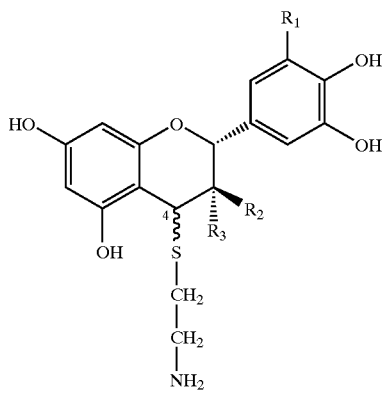

where $R_1$=OH, $R_2$=H, $R_3$=OH, and the compound is a 4ξ-(2-aminoetiltio)epigalocatechine.

8. A product comprising the compound of claim 7, wherein the compound is a 4-α-(2-aminoethylthio) epigalocatechine, and (b) a 4-β-(2-aminoethylthio) epigalocatechine of formula IV or a salt thereof.

9. A compound having the following formula V or a salt thereof:

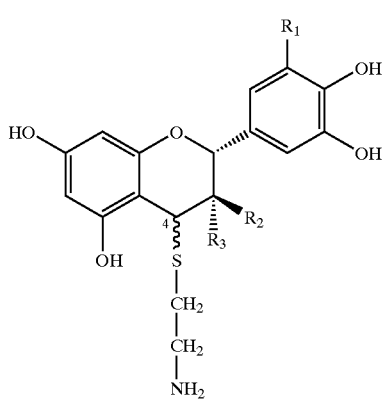

where $R_1$=OH, $R_2$=OH, $R_3$=H, and the compound is a 4ξ-(2-aminothylthio)galocatechine.

10. A product comprising (a) the compound of claim 9, wherein the compound is a 4-α-(2-aminoethylthio) galocatechine; and (b) a 4-β-(2-aminoethylthio) galocatechine of formula V or a salt thereof.

11. A compound having the following formula VI or a salt thereof:

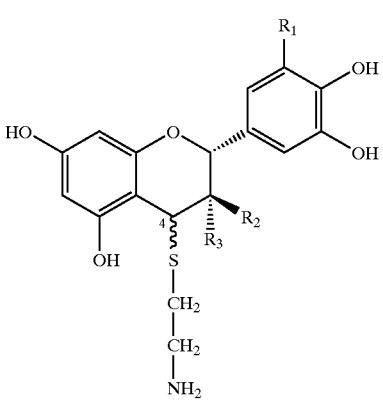

where $R_1$=OH, $R_2$=H, $R_3$ is

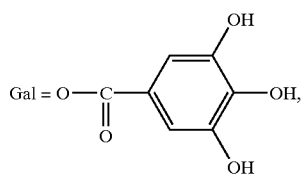

and the compound is a 4ξ-(2-aminoethylthio) epigalocatechine-3-O-galate.

12. A product comprising (a) the compound of claim 11, wherein the compound is a 4-α-(2-aminoethylthio) epigalocatechine-3-O-galate, and (b) a 4-β-(2-aminoethylthio)epigalocatechine-3-O-galate of formula VI or a salt thereof.

13. A process for preparing a compound of formula I, II, III, IV, V or VI or a salt of the compound of formula I, II, III, IV, V or VI:

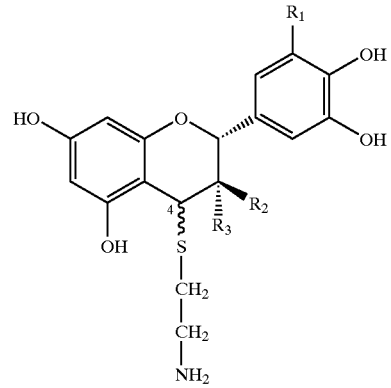

wherein

I $R_1$=H, $R_2$=H, $R_3$=OH, and the compound is a 4ξ-(2-aminoethylthio)epicatechine; or II $R_1$=H, $R_2$=OH, $R_3$=H, and the compound is a 4ξ-(2-aminoethylthio)catechine; or III $R_1$=H, $R_2$=H, $R_3$=Gal, and the compound is a 4ξ-(2-aminoethylthio)epicatechine-3-O-galate; or IV $R_1$=OH, $R_2$=H, $R_3$=OH, and the compound is a 4ξ-(2-aminoetiltio)epigalocatechine; or V $R_1$=OH, $R_2$=OH, $R_3$=H, and the compound is a 4ξ-(2-aminoethylthio)galocatechine; or VI $R_1$=OH, $R_2$=H, $R_3$=Gal, and the compound is a 4ξ-(2-aminoethylthio) epigalocatechine-3-O-galate;

wherein

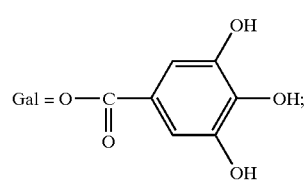

said process comprising the steps of
  (a) extracting polyphenols from a plant source to obtain a polyphenol extract;
  (b) subjecting the extract to thioacidolysis in the presence of cysteamine and an acid with formation of a reaction mixture; and
  (c) washing and isolating the compound from the reaction mixture with use of a cationic exchange resin.

14. The process of claim 13, wherein step (c) comprises eluting the compound from a column comprising the cationic exchange resin in the presence of a mixture comprising water, salt and a solvent, the solvent being selected from the group consisting of methanol, ethanol, acetonitrile and tetrahydrofurane.

15. A method for administering an antioxidant to a subject comprising:
  (a) providing a cosmetic or pharmaceutical product that comprises a compound of the formula I–VI or a salt of the compound of formula I–VI:

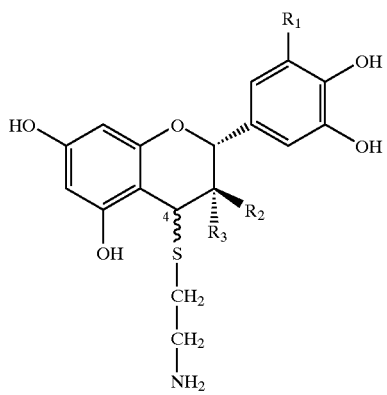

wherein

I $R_1$=H, $R_2$=H, $R_3$=OH, and the compound is a 4ξ-(2-aminoethylthio)epicatechine; or II $R_1$=H, $R_2$=OH, $R_3$=H, and the compound is a 4ξ-(2-aminoethylthio)catechine; or III $R_1$=H, $R_2$=H, $R_3$=Gal, and the compound is a 4ξ-(2-aminoethylthio)epicatechine-3-O-galate; or IV $R_1$=OH, $R_2$=H, $R_3$=OH, and the compound is a 4ξ-(2-aminoetiltio)epigalocatechine; or V $R_1$=OH, $R_2$=OH, $R_3$=H, and the compound is a 4ξ-(2-aminoethylthio)galocatechine; or VI $R_1$=OH, $R_2$=H, $R_3$=Gal, and the compound is a 4ξ-(2-aminoethylthio) epigalocatechine-3-O-galate;

wherein

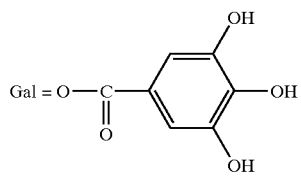

(b) administering an effective amount of the cosmetic or pharmaceutical product to the subject.

* * * * *